(12) United States Patent
Wilson

(10) Patent No.: US 7,731,709 B2
(45) Date of Patent: Jun. 8, 2010

(54) OPTICAL HEIGHT ZEROING DEVICE

(75) Inventor: Stephen Ferrer Wilson, North Easton, MA (US)

(73) Assignee: Codman & Shurtleff, Inc., Raynham, MA (US)

(\*) Notice: Subject to any disclaimer, the term of this patent is extended or adjusted under 35 U.S.C. 154(b) by 22 days.

(21) Appl. No.: 11/839,211

(22) Filed: Aug. 15, 2007

(65) Prior Publication Data

US 2007/0293847 A1    Dec. 20, 2007

Related U.S. Application Data

(60) Division of application No. 11/081,411, filed on Mar. 16, 2005, now Pat. No. 7,354,431, which is a continuation of application No. 10/113,803, filed on Mar. 29, 2002, now Pat. No. 6,881,210.

(51) Int. Cl.
  *A61M 1/00* (2006.01)
(52) U.S. Cl. ............... 604/540; 33/273; 33/281; 33/290; 33/292; 33/379; 604/541; 604/322; 604/127; 600/561; 606/15; 606/2
(58) Field of Classification Search ......... 604/540, 604/541, 322, 127; 33/273, 281, 290, 292, 33/379; 600/561; 606/15, 2
See application file for complete search history.

(56) References Cited

U.S. PATENT DOCUMENTS

| | | | |
|---|---|---|---|
| 2,968,228 A * | 1/1961 | Merritt | 396/50 |
| 3,552,395 A | 1/1971 | Bidwell et al. | |
| 3,690,312 A * | 9/1972 | Leibinsohn | 600/487 |
| 3,996,927 A * | 12/1976 | Frank | 600/486 |
| 4,846,173 A * | 7/1989 | Davidson | 606/130 |
| 5,102,391 A | 4/1992 | Palestrant | |
| 5,168,633 A * | 12/1992 | Harrison et al. | 33/512 |
| 5,280,789 A * | 1/1994 | Potts | 600/486 |

(Continued)

OTHER PUBLICATIONS

Product Literature, by Pudenz-Schulte Medical Corporation; Becker EDMS II, External Drainage and Monitoring System; Sep. 1991.

(Continued)

*Primary Examiner*—Tatyana Zalukaeva
*Assistant Examiner*—Ginger T Chapman
(74) *Attorney, Agent, or Firm*—Nutter McClennen & Fish LLP

(57) ABSTRACT

A leveling device for determining the zero pressure point of an external draining system with respect to a patient is provided. The leveling device generally includes a body having a viewing element defining a field of vision, and a reference point indicator spaced apart from the viewing element and disposed within the line of vision. The viewing element and the reference point indicator define a line of sight. The device further includes a horizontal level indicator mated to the body and oriented parallel to the line of sight established by the viewing element and the reference point indicator. The horizontal level indicator is effective to indicate the horizontal alignment of the body with respect to a particular reference point viewed through the viewing element and indicated by the reference point indicator. The device can optionally include a reflector element disposed adjacent the horizontal level indicator and within the field of vision, such that the horizontal level indicator is visible through the viewing element via the reflector element.

4 Claims, 5 Drawing Sheets

U.S. PATENT DOCUMENTS

| | | |
|---|---|---|
| 5,752,520 A | 5/1998 | Bisnaire et al. |
| 5,772,625 A * | 6/1998 | Krueger et al. ............... 604/9 |
| 6,277,109 B1 | 8/2001 | Harper et al. |
| 6,290,694 B1 | 9/2001 | Harper et al. |
| 6,881,210 B2 | 4/2005 | Wilson |
| 7,354,431 B2 * | 4/2008 | Wilson ..................... 604/540 |
| 2001/0011166 A1 | 8/2001 | Harper et al. |

OTHER PUBLICATIONS

Product Literature, by Medtronic; exacta, Reusable Disposable Drainage System, 1999.

Product Literature, by Integra NeuroCare, External Drainage Systems.

Product Literature, by Codman, Drainage/Monitering External Drainage.

* cited by examiner

OPTICAL HEIGHT ZEROING DEVICE

CROSS-REFERENCE TO RELATED APPLICATIONS

This application is divisional application of U.S. application Ser. No. 11/081,411 now U.S. Pat. No. 7,354,431, filed on Mar. 16, 2005, and entitled "Optical Height Zeroing Device," which is a continuation of application Ser. No. 10/113,803 (now U.S. Pat. No. 6,881,210), filed Mar. 29, 2002, and entitled "Optical Height Zeroing Device," now U.S. Pat. No. 6,881,210. These references are hereby incorporated by reference in their entireties.

FIELD OF THE INVENTION

The present invention relates to a device for controlling intracranial pressure, and in particular to a leveling device for determining the zero pressure point of an external draining system with respect to a patient.

BACKGROUND OF THE INVENTION

Cerebrospinal fluid (CSF) is a clear, colorless fluid that is primarily produced by the choroid plexus and surrounds the brain and spinal cord. CSF constantly circulates through the ventricular system of the brain and is ultimately absorbed into the bloodstream. CSF has three important functions. First, because CSF keeps the brain and spinal cord buoyant, it acts as a protective cushion or "shock absorber" to prevent injuries to the central nervous system. Second, CSF acts as the vehicle through which nutrients are delivered to the brain, and conversely, as the vehicle through which waste products are carried away from the brain tissue. Finally, by flowing between the cranium and the spine, CSF can compensate for changes in the amount of blood found in the brain.

Hydrocephalus is a neurological condition that is caused by the abnormal accumulation of CSF within the ventricles, or cavities, of the brain. Hydrocephalus, which affects mostly infants and young children, arises when the production of CSF exceeds the absorption of CSF into the bloodstream. This is usually the result of some type of blockage in the brain that prevents the normal flow of fluid. Such blockage can be caused by a number of factors, including, for example, genetic predisposition, intraventricular or intracranial hemorrhage, infections such as meningitis, head trauma, or the like. Blockage of the flow of CSF consequently creates an imbalance between the amount of CSF produced by the choroid plexus and the rate at which CSF is absorbed into the bloodstream, thereby increasing pressure within the ventricles in the brain, which causes the ventricles to enlarge.

Hydrocephalus is often treated by draining cerebrospinal fluid accumulated in the ventricles from the brain using a hydrocephalus shunt catheter inserted through the skull and into the ventricles. The catheter drains the fluid away from the brain and delivers it to another part of the body, such as the peritoneum or the superior vena cava. The catheter may employ a flow-limiting device such as a differential pressure valve, referred to as a shunt valve, to maintain a physiological pressure within the ventricles.

Prior to implantation of a hydrocephalus shunt, an external drainage system is used to control pressure within the ventricles. External drainage systems are also used to assess patient response to CSF drainage, to evaluate the brain compliance to determine the appropriate shunt pressure setting, to treat infection, to drain blood laden CSF, to monitor intracranial pressure (ICP), and while awaiting patient stabilization. External drainage systems typically include a support member, e.g., an IV pole, having a moveable drip assembly with a disposable bag adjustably fastened to the support. The flow of cerebrospinal fluid from the patient's brain can be controlled by elevating or lowering the drip assembly to alter the resistance of the fluid pathway from the brain ventricles into the drip assembly. This provides a means of controlling the pressure within the ventricles.

External drainage systems are often provided with a scale movably mated to the support member for determining and controlling the ICP of the fluid in the patient's ventricles. In order for the scale to accurately reflect the true ICP of the patient, a zero pressure point on the scale must be aligned at the same height as a zero reference point on the patient, such as a point corresponding to the position of the patient's Foramen of Monro. Because this is not a visible point, the external auditory canal is often used as a convenient external landmark. Once the zero pressure point on the scale is determined by aligning the zero pressure point on the scale with this landmark, the drip assembly can be adjusted with respect to the zero pressure point in order to control the flow of fluid from the patient's ventricular system into the drip assembly, and thereby control ICP.

A variety of techniques for measuring and aligning the zero reference point on the patient with the zero pressure point on the scale are known. Laser pointers, for example, are used by attaching the laser pointer to the scale on the EDS, or positioning it adjacent the scale. The laser is then activated, and the height of the laser is adjusted until the laser light aligns with a zero reference point on the patient, such as a position corresponding to the auditory canal. The zero pressure point on the scale is then marked, or alternatively the scale is positioned to align the zero pressure point marked on the scale with the zero reference point on the patient, for the duration of use of the external drainage system. The drip assembly can then be adjusted with respect to that reference pressure point in order to increase or decrease the ICP, and thereby increase or decrease the flow of fluid from the patient's brain. While such laser devices have proven effective, it can be difficult to ensure that the laser beam is horizontally level. Additional drawbacks of laser devices include the costs and need to power such devices, as well as any potential risks that may result from shining a laser beam directly at a patient.

Another prior art device that is used for determining the zero pressure point is a telescoping antenna with a leveling bubble. The antenna is extended from the support member to the zero reference point on the patient, and the leveling bubble is used to horizontally position the antenna. Another similar prior art device is a large L- or T-square which is held perpendicular with respect to the vertical support member, and horizontal with respect to the patient. Drawbacks of these devices include the need for the patient to be relatively close to the support member, as well as the possible risk of injuring a patient with the device while positioning the device adjacent the patient's zero reference point. Such devices can also be awkward to handle, as they often require one person to hold the T- or L-square, while another person adjusts the height of the drainage system. Moreover, T- and L-square devices are often very large, and require sizable storage spaces.

Accordingly, there exists a need for a safe, accurate, and easy to use leveling device for determining the zero pressure point of an external draining system with respect to a patient.

SUMMARY OF THE INVENTION

The present invention provides a leveling device for determining the zero pressure point of an external draining system with respect to a patient. The leveling device generally includes a body having a viewing element defining a field of vision, and a reference point indicator spaced apart from the viewing element and disposed within the line of vision. The viewing element and the reference point indicator define a line of sight. The device further includes a horizontal level indicator mated to the body and oriented parallel to the line of sight established by the viewing element and the reference point indicator. The horizontal level indicator is effective to indicate the horizontal alignment of the body with respect to a particular reference point viewed through the viewing element and indicated by the reference point indicator.

In one embodiment, the device includes a reflector element disposed adjacent the horizontal level indicator and within the field of the vision. The reflector element is preferably disposed at an angle with respect to the horizontal level indicator and the viewing element, such that the horizontal level indicator is visible through the viewing element via the reflector element.

The device can have a variety of configurations. In an exemplary embodiment, the reference point indicator is formed from a rigid member having a tip formed thereon for indicating the reference point, and the body of the device is adapted to be mated to a portion of an external drainage system, and in particular to a scale on an external drainage system. In one embodiment, the body can be adapted to be adjusted in both a horizontal direction and vertical direction with respect to the scale. The leveling device can also optionally include a viewing element that extends outward from the body and includes a bore extending therethrough. A lens can optionally be disposed within the bore of the viewing element.

In other aspects of the present invention, a method of adjusting the pressure of an external medical fluid drainage system is provided. The external fluid drainage system includes a support member, a scale movably mated to the support member, a drip assembly mated to the scale, and a catheter extending from the drip assembly to a fluid drainage point in a patient's cerebrospinal fluid system. The method includes the step of providing a leveling device including a body having a viewing element defining a field of vision, and a reference point indicator spaced apart from and disposed within the field of vision of the viewing element. The viewing element and reference point indicator define a line of sight. A horizontal level indicator is mated to the body and disposed parallel to the line of sight established by the viewing element and the reference point indicator. The horizontal level indicator is effective to indicate the horizontal alignment of the body with respect to a particular reference point viewed through the viewing element and indicated by the reference point indicator thereby establishing the same vertical height for the body and the particular reference point. The method further includes the steps of aligning the body horizontally using the horizontal level indicator, determining the reference point on the patient, viewing the reference point through the viewing element, and vertically aligning the reference point indicator with the reference point while maintaining the horizontal alignment of the body, and thereby establishing a zero reference point. The zero reference point is preferably the position at which the pressure differential between the patient's cerebrospinal fluid system and the fluid drainage system is zero. In a further embodiment, the method can include the step of adjusting the drip assembly with respect to the zero reference point to change the pressure differential.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a leveling device for vertically aligning two objects positioned at a distance apart from one another. More particularly, a leveling device for use with an external drainage system is provided. The leveling device is effective to determine and set the zero pressure point on an external draining system with respect to a patient. The zero pressure point is the point at which the ICP is zero, and thus the pressure differential between the patient's cerebrospinal fluid system and an external drainage system is zero. Once the zero pressure point is determined, the ICP can be adjusted to accurately control the flow of fluid from the patient to the external drainage system.

Figure 1:
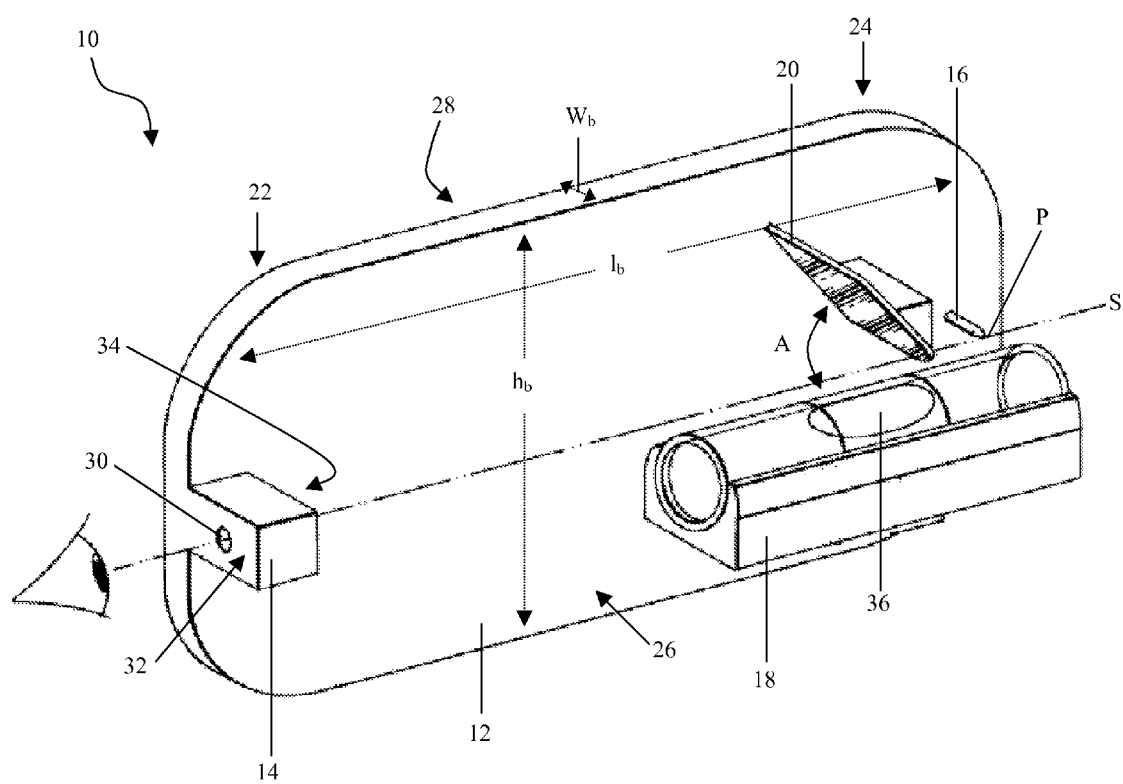
FIG. 1 is a perspective view illustration of a leveling device according to one embodiment of the present invention.
Figure 2:
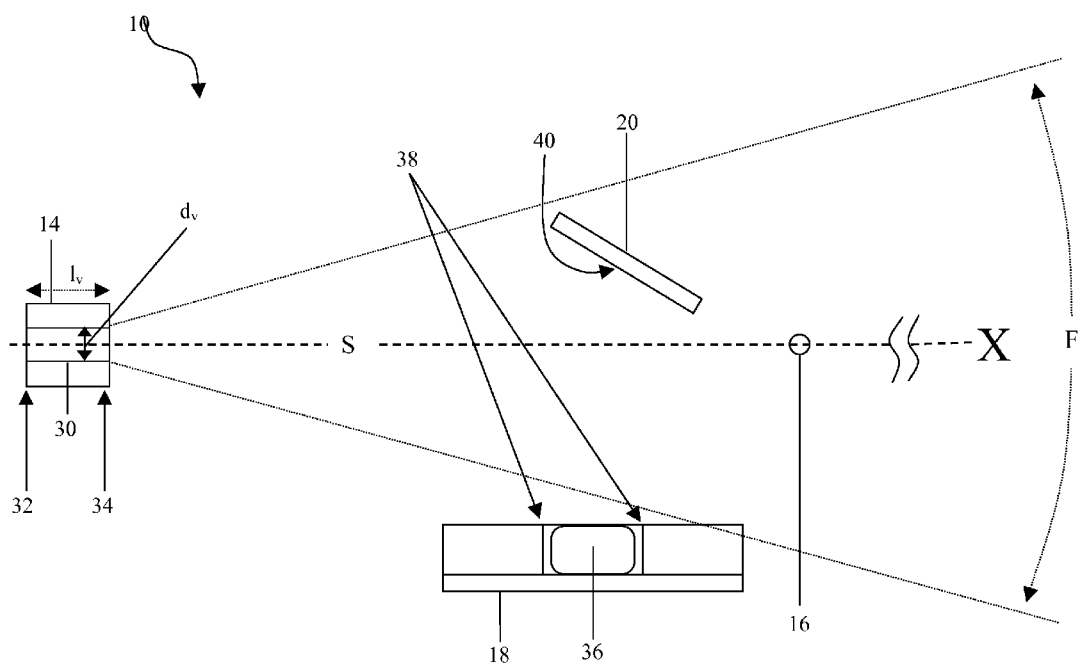
FIG. 2 is a side view schematic illustration of the components of the leveling device of FIG. 1.

As shown in FIGS. 1 and 2, the device 10 generally includes a body 12 having a viewing element 14 defining a field of vision F, and a reference point indicator 16 spaced apart from the viewing element 14 and disposed within the field of vision F. The viewing element 14 and the reference point indicator 16 define a line of sight S. The device 10 further includes a horizontal level indicator 18 mated to the body 12 and oriented parallel to the line of sight S established by the viewing element 14 and the reference point indicator 16. The horizontal level indicator 18 is effective to indicate the horizontal alignment of the body 12 with respect to a particular reference point X viewed through the viewing element 14 and indicated by the reference point indicator 16. The device 10 can also optionally include a reflector element 20 disposed adjacent the horizontal level indicator 18 and within the field of vision F. The reflector element 20 is disposed at an angle A with respect to the horizontal level indicator 18 and the viewing element 14, such that the horizontal level indicator 18 is visible through the viewing element 14 via the reflector element 20.

The body 12 of the device 10, shown in FIG. 1, can have a variety of configurations, but is preferably a rigid member that is configured to support the viewing element 14, the reference point indicator 16, the horizontal level indicator 18, and optionally the reflector element 20. While the body 12 can have virtually any configuration, shape and size, FIG. 1 illustrates an exemplary embodiment of a body 12 having a generally rectangular shape, and including a proximal end 22, a distal end 24, a front surface 26, and a back surface 28. The body 12 includes a length $l_b$, width $w_b$, and height $h_b$ which can vary, but preferably the body 12 has a length $l_b$ in the range of about 40 to 80 mm, a width $w_b$ in the range of about 3 to 10 mm, and height $h_b$ in the range of about 30 to 100 mm.

The components 14, 16, 18, 20 of the device 10 can be mated to any portion of the body 12, but are preferably disposed on the front surface 26 of the body 12. The components 14, 16, 18, 20 can be formed integrally with the body 12, or they can be mated to the device 10 using a variety of attachment mechanisms including, for example, a rivet, screw, snap, buckle, adhesive, or similar attachment mechanism.

Figure 5:
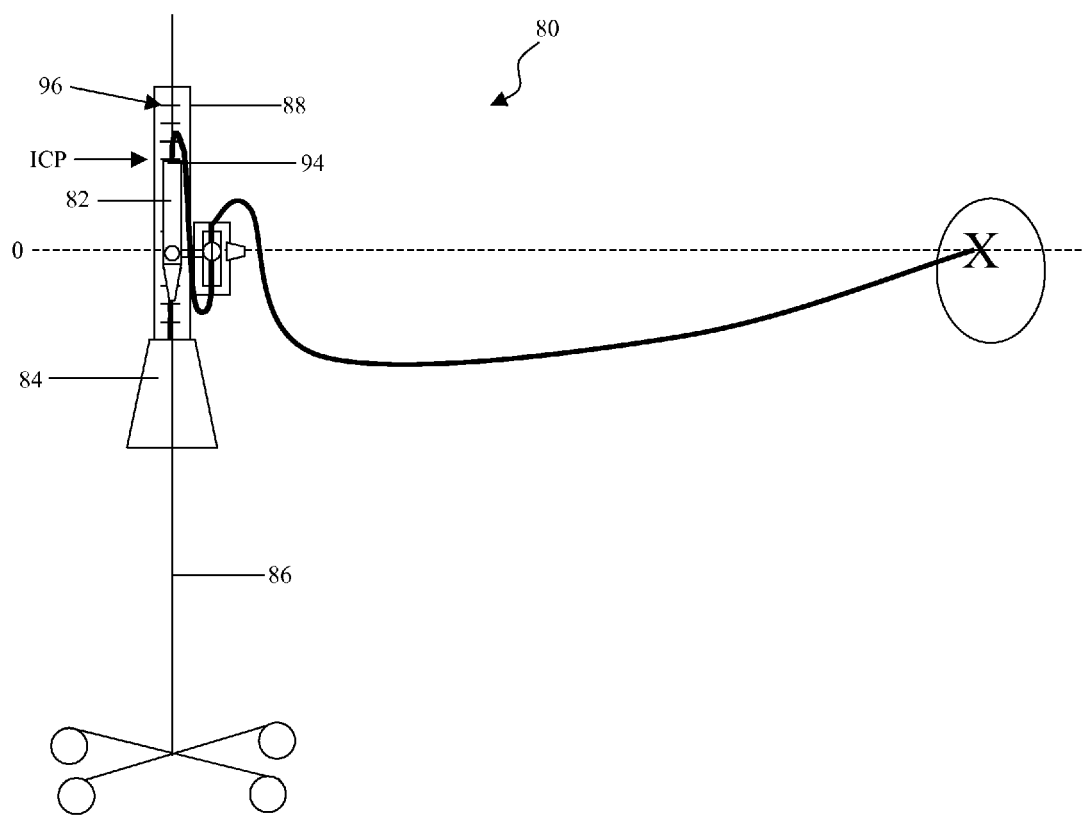
FIG. 5 is a schematic illustration of an external drainage system having a zero pressure point indicated on the scale, and having an adjusted ICP.

The back surface 28 of the body 12 can be a substantially flat surface, or alternatively can include a mating element (not shown) for mating the body 12 to an external drainage system 80 as shown in FIGS. 5 and 6. In an exemplary embodiment, the body 12 is adapted to be removably mated to a support member 86 of an external drainage system 80, and in particular to a scale 88 that is movably mated to a support member 86. The body 12 can be adjustable in both a horizontal direction and a vertical direction with respect to the scale 88. A person having ordinary skill in the art will appreciate that a variety of mating techniques can be utilized for removably mating the body 12 to the scale 88. By way of non-limiting example, a clamp, screw assembly, buckle, snap, or similar attachment device can be used to mate the body 12 to the scale 88. The back surface 28 of the body 12 can also optionally or alternatively include a handle (not shown) for grasping and manipulating the device 10. A person having ordinary skill in the art will appreciate that the handle can have any shape or configuration, and should be adapted to facilitate gripping of the device 10.

Referring back to FIGS. 1 and 2, the device 10 includes a viewing element 14 mated to, or integrally formed with, the body 12, and preferably positioned on the front surface 26 at or near the proximal end 22 of the body 12. The viewing element 14 can have a variety of configurations, but preferably extends outward from the front surface 26 of the body 12, and includes a bore 30 extending therethrough. The bore 30 extends from a proximal end 32 to a distal end 34 of the viewing element 14, and defines a field of vision F (FIG. 2) that can be viewed by a person looking through the bore 30 in the viewing element 14. The viewing element 14 can optionally include a lens (not shown) disposed within the bore 30 for viewing and optionally for magnifying objects viewed through the bore 30. The shape and size of the bore 30 can vary, but preferably the bore 30 has a diameter $d_v$ and length $l_v$ that is sufficient to define a field of vision F within which the components 16, 18, 20 of the device 10 and the object X can be viewed. In an exemplary embodiment, the bore 30 has a diameter $d_v$ in the range of about 3 to 20 mm, and a length $l_v$ in the range of about 1 to 100 mm. A person having ordinary skill in the art will appreciate that the viewing element 14 can have a variety of configurations, and a variety of different types of viewing elements can be utilized with the present invention. For example, the viewing element can be formed from a scope or similar type of device.

The device 10 further includes a reference point indicator 16 that can be viewed through the viewing element 14, and that is effective to provide a reference point P which can be used to reference a particular reference point of an object X positioned at a distance from the device 10. The reference point indicator 16 is preferably formed from a rigid member, such as a pin or screw, that extends outward from the front surface 26 of the body 12 and forms a substantially sharp reference point P. The reference point indicator 16 is preferably positioned at or near the distal end 24 of the body 12, and within the field of vision F defined by the viewing element 14. In use, the reference point indicator 16 and the viewing element 14 define a horizontal line of sight S, which is used to align the device 10 horizontally with respect to an object X viewed through the viewing element 14 and positioned at a distance from the device 10.

A person having ordinary skill in the art will appreciate that the reference point indicator 16 can have a variety of configurations. By way of non-limiting example, the reference point indicator can include a cylindrical o-shaped member, rather than a sharp pointed tip P. Alternatively, the reference point indicator can be formed integrally with the viewing element 14. For example, where the viewing element 14 includes a lens (not shown) disposed within the bore 30, a marking can be formed on the lens to provide a reference point P. In use, a person looking through the viewing element 14 can align the reference point P on the lens with an object X viewing through the viewing element 14 and positioned at a distance from the device 10.

The device 10 of the present invention further includes a horizontal level indicator 18 mated to the body 12 and oriented parallel to the line of sight S established by the viewing element 14 and the reference point indicator 16. The horizontal level indicator 18 is effective to indicate the horizontal alignment of the device 10, and in particular the horizontal alignment of the line of sight S. The horizontal level indicator 18 can be mated to any portion of the body 12, but is preferably mated to the front surface 26 of the body 12, and is preferably positioned between the reference point indicator 16 and the viewing element 14 just below the line of sight S. In an exemplary embodiment, the horizontal level indicator 18 is disposed outside of the field of vision F, and thus cannot be viewed through the viewing element 14.

Horizontal level devices are well known in the art, and a variety of different devices can be used to indicate the horizontal level of the device 10 of the present invention. The most common type of horizontal level indicator, shown in FIG. 1, is a liquid-filled tube that has a small air bubble 36 trapped therein. Because liquids always seek their own level, the bubble 36 will be centered in the tube, as indicated by the markings 38, when the tube is held level. A person having ordinary skill in the art will appreciate that virtually any type of horizontal level indicator device can be used with the device 10 of the present invention.

Figure 3:
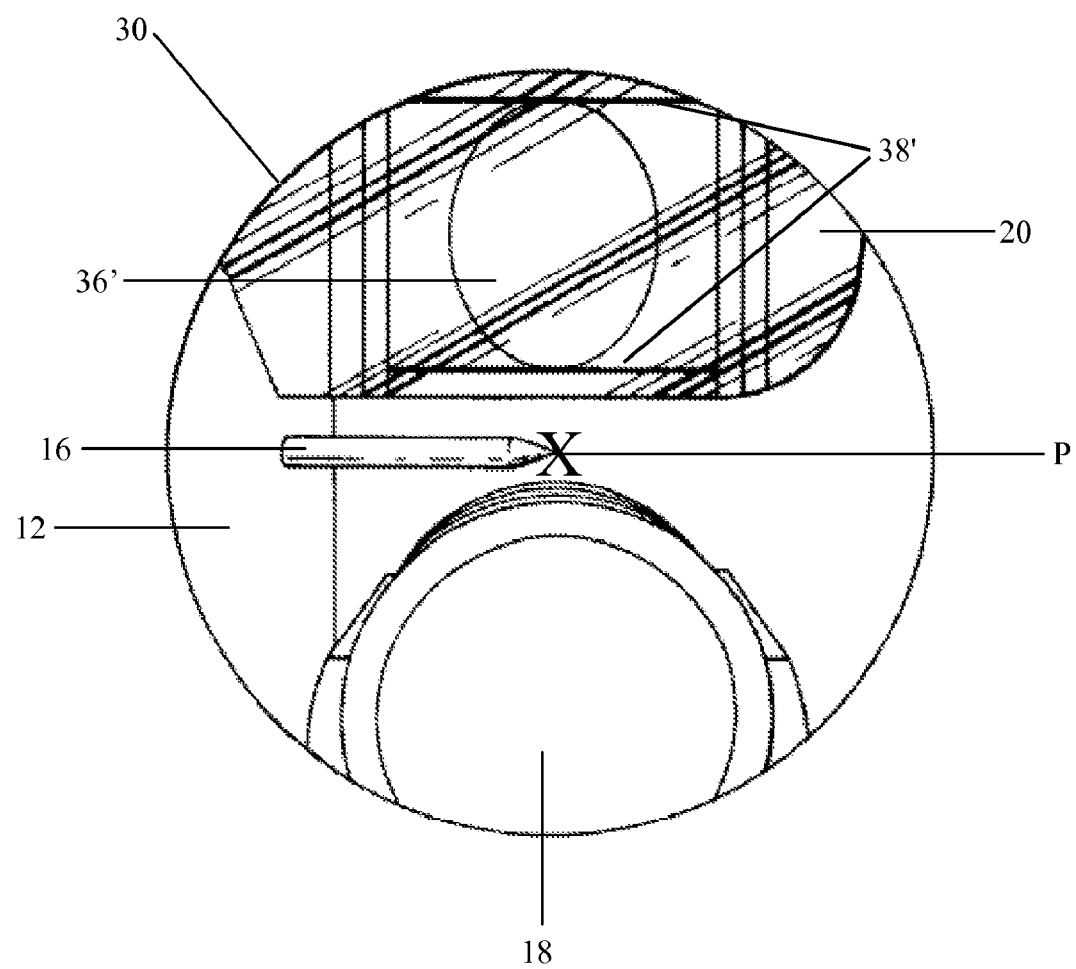
FIG. 3 is an illustration of the leveling device of FIG. 1 as viewed through a viewing element disposed on the device.

The device 10 can also optionally include a reflector element 20 for facilitating viewing of the horizontal level indicator 18, particularly when the level indicator 18 is positioned outside of the field of vision F. The reflector element 20 includes a reflective surface 40, and is disposed adjacent the horizontal level indicator 18 and within the field of vision F. In the embodiment shown in FIGS. 1-3, the reflector element 20 is disposed on the front surface 26 of the body 12 between the reference point indicator 16 and the viewing element 14, and just above the line of sight S. The reflective surface 40 is preferably disposed at an angle with A with respect to the horizontal level indicator 18 and the viewing element 14, such that the horizontal level indicator 18 is visible through the viewing element 14 via the reflector element 20, as shown in FIG. 3. In an exemplary embodiment, the angle A is between about 25° and 75°, and more preferably is about 45°. The size, surface curvature, and shape of the reflector element 20 can also vary, but the reflector element 20 should have a size sufficient to provide a reflection of the markings 38 on the horizontal level indicator 18, and the space between the markings 38. In use, as shown in FIG. 3, the reflector element 20 can be viewed through the viewing element 14, and is effective to provide a reflected image of the markings 38' on the horizontal level indicator 18, as well as the air bubble 36' when positioned between the markings 38'.

A person having ordinary skill in the art will appreciate that, while FIGS. 1-2 illustrate one embodiment of a leveling device 10, the device 10 can have a variety of configurations, shapes, and sizes. For example, the horizontal level indicator can be positioned virtually anywhere on the body 12, or alternatively can be mated to a separate device, such as an external drainage system, for use with the leveling device 10. Moreover, the device 10 can be directly mated to some object other than a body 12. For example, the components 14, 16, 18, 20 can be directly mated to an external drainage system, and in particular to a scale on an external drainage system, thereby eliminating the need for a body 12 altogether.

In use, the device 10 is effective to indicate the horizontal alignment of the body 12 with respect to a particular reference point X viewed through the viewing element 14 and indicated by the reference point P on the reference point indicator 16. As shown in FIG. 3, a person looking through the bore 30 in the viewing element 14 can see the reference point indicator 16, as well as the reflected image of the horizontal level indicator 18 in the reflector element 20. The reference point indicator 16 is used to align the reference point P with an object X positioned at a distance apart from the device 10. Simultaneously, the horizontal level indicator 18 is adjusted until the air bubble 36 is positioned between the markings 38 on the horizontal level indicator 18, as shown in the reflected image. The horizontal alignment of the body 12 with respect to a particular reference point X is thus determined.

Figure 4:
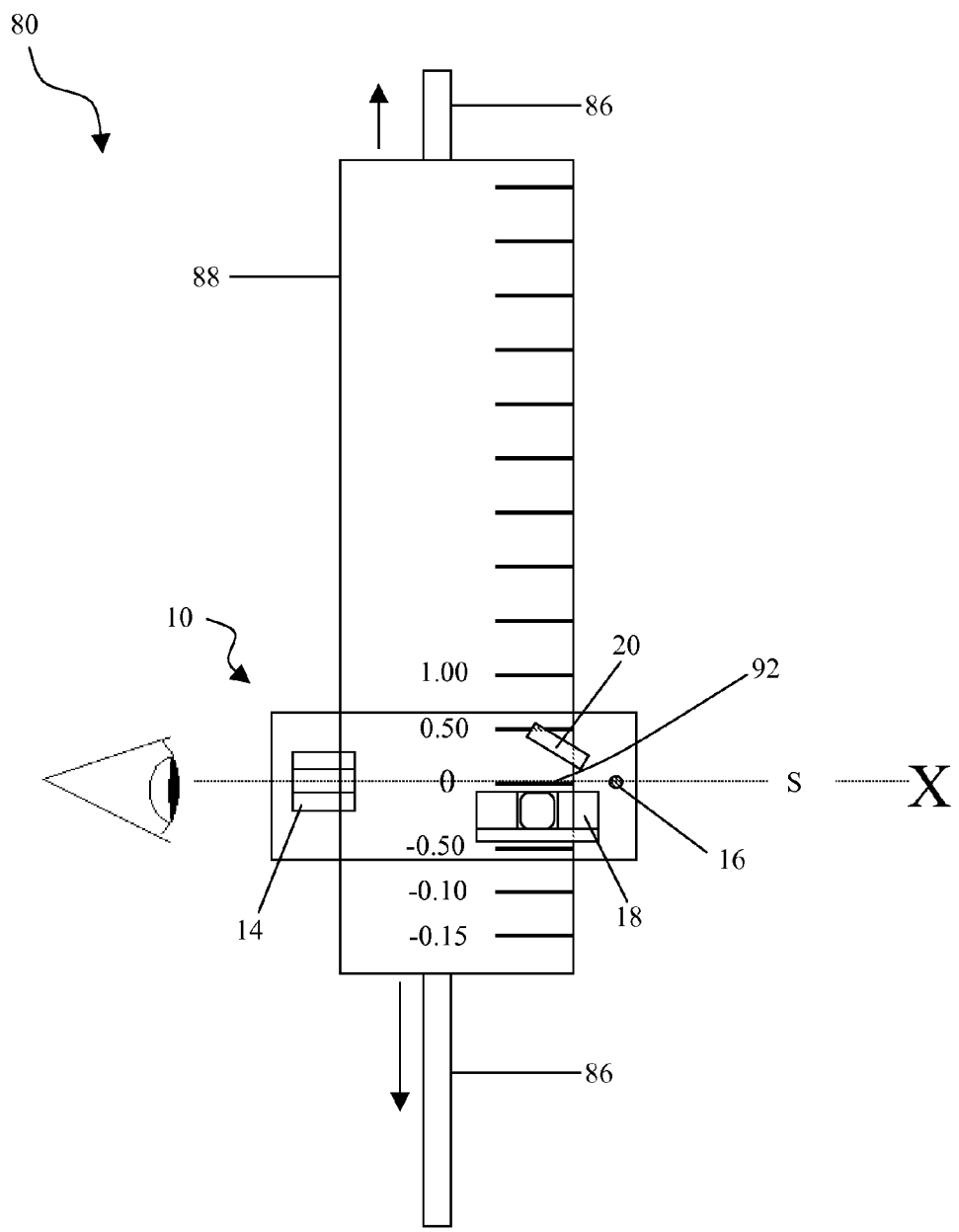
FIG. 4 is a schematic illustration of a leveling device attached to a scale on an external drainage system, according to another embodiment of the present invention.

In an exemplary embodiment, shown in FIGS. 4 and 5, the device 10 of the present invention is used to determine the zero pressure point 92 of an external drainage system 80. FIG. 5 illustrates a typical external drainage system 80 having a support member 86, a scale 88 mated to or formed on the support member 86, a drip chamber 82 for collecting CSF drainage, and a collection bag 84 for receiving fluid from the drip chamber 82. In an exemplary embodiment, the scale 88 is slidably movable along the axis of the support member 86. The collection bag 84 is preferably fixed to the support member 86, while the drip chamber 82 is slidably movable in a vertical direction with respect to the scale 88. A person having ordinary skill in the art will appreciate that the medical drainage system 80 can have a variety of configurations.

Referring the FIG. 4, the leveling device 10 is removably attached to the scale 88 such that the line of sight S, defined by the viewing element 14 and the reference point indicator 16, is aligned with the zero mark 92 on the scale. The zero pressure point 92 can be determined by viewing the reference point indicator 16 and the horizontal level indicator 18 through the bore 30 in the viewing element 14. The horizontal level of the device 10 is adjusted by viewing the reflection of the markings 38' on the horizontal level indicator 18 through the reflector element 20, and positioning the bubble 36' on the horizontal level indicator 18 between the markings 38'. This can be accomplished by rotating either the scale 88 with respect to the support member 86, or alternatively rotating the leveling device 10 with respect to the scale 88. Once the horizontal level is adjusted, the reference point P on the reference point indicator 16 is vertically aligned with the reference point on an object X, preferably a patient's external auditory canal, positioned at a distance from the device 10. The alignment is preferably adjusted by sliding the scale 88, with the leveling device 10 mated thereto, in a vertical direction. Once the device 10 is horizontally and vertically level with respect to the particular reference point of object X, the scale 88 is locked or fixed into position, thereby aligning the zero mark 92 on the scale 88 with the patient's external auditory canal. As a result, the zero mark 92 on the scale 88 accurately reflects the zero pressure point, and thus the ICP, of the external drainage system 80 with respect to the patient. The ICP of the external drainage system 80 can then be adjusted, as shown in FIG. 5, by moving the drip chamber 82 to position the top of the drip chamber 94 adjacent the desired ICP, as indicated by the indicia 96 on the scale.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for indicating a horizontal alignment of a body with respect to a target, comprising:
    viewing a reference point indicator, a horizontal level indicator, and a target through a viewing element of a leveling device; and
    vertically aligning the leveling device with the target using the reference point indicator while simultaneously aligning the leveling device horizontally using the horizontal level indicator;
    wherein the leveling device is coupled to an external drainage system and is effective to determine a zero-pressure point of the external drainage system.

2. The method of claim 1, wherein the horizontal level indicator is viewed through the viewing element on a reflector element.

3. The method of claim 1, wherein the leveling device is horizontally aligned by moving a bubble between two markings on the horizontal level indicator.

4. The method of claim 1, wherein vertically aligning the leveling device comprises sliding the leveling device relative to a vertical support on which the leveling device is mounted.

* * * * *